United States Patent [19]

Bidney

[11] Patent Number: 5,932,782

[45] Date of Patent: Aug. 3, 1999

[54] PLANT TRANSFORMATION METHOD USING AGROBACTERIUM SPECIES ADHERED TO MICROPROJECTILES

[75] Inventor: Dennis Bidney, Des Moines, Iowa

[73] Assignee: Pioneer Hi-Bred International, Inc., Des Moines, Iowa

[21] Appl. No.: 07/614,403

[22] Filed: Nov. 14, 1990

[51] Int. Cl.$^6$ ....................................................... A01H 1/04
[52] U.S. Cl. ........................................ 800/296; 435/172.3
[58] Field of Search ................................ 435/172.3, 176; 935/85, 56; 800/205

[56] References Cited

U.S. PATENT DOCUMENTS

| | | | |
|---|---|---|---|
| 4,647,537 | 3/1987 | Shigemitsu | 435/178 |
| 4,771,002 | 9/1988 | Gelvin | 435/6 |
| 4,859,377 | 8/1989 | Shasha et al. | 264/4.1 |
| 4,945,050 | 7/1990 | Sanford et al. | 435/459 |

FOREIGN PATENT DOCUMENTS 0301749  2/1989  European Pat. Off. ........ C12N 15/00

OTHER PUBLICATIONS

Graves et al 1986 Plant Molec Biol 7 : 43–50.
Engstrom et al 1987. J Molec Biol 197 : 635–645.
Klein et al 1988 Bio/Technology 6 : 559–563.
Sanford 1988 trends in Biotech 6 :299–302.

*Primary Examiner*—James Ketter

[57] ABSTRACT

Bacteria of the species Agrobacterium are applied to particles which are used in a typical particle gun in a manner which retains their viability after the dry-down process involved in microparticle bombardment. When plant materials are bombarded with particles coated with the bacteria, high rates of stable transformation are achieved.

11 Claims, 4 Drawing Sheets

5,932,782

PLANT TRANSFORMATION METHOD USING AGROBACTERIUM SPECIES ADHERED TO MICROPROJECTILES

TECHNICAL FIELD

The present invention relates to the use of Agrobacterium species for the transformation of plants.

BACKGROUND

Much research in plant molecular biology is now directed to the improvement of plant varieties via use of recombinant DNA techniques. Historically, plant breeders used classical genetic techniques to identify, preserve and crossbreed varietal lines having desirable traits. More recently, new plant varieties were induced by chemicals or by radiation treatment to mutate plant cells which were then regenerated using tissue culture techniques. These random and unpredictable approaches have obvious drawbacks. By the use of recombinant DNA technology, specific genes producing specific proteins, such as those imparting insect resistance, can be introduced into a plant to produce a desired variety with a particular trait.

Plants have been transformed using a variety of methods. A common method for transformation of dicotyledonous plants has been the use of disarmed Agrobacterium species, which are relatively benign natural pathogens of dicotyledonous plants. Agrobacteria infect plants and cause a callus of tumor tissue to grow in an undifferentiated way at the site of infection. The tumor inducing agent is the Ti plasmid, which functions by integrating some of its DNA into the genome of host plant cells. This plasmid is an ideal vector for transformation of plants. The portion of the Ti plasmid DNA that is transferred to host cell chromosomes during Agrobacterium infection is referred to as transforming ("T") DNA. See, for example, Watson JD, Tooze J, & Kurtz DT, *Recombinant DNA: A Short Course*, 169 (W. H. Freeman, 1983).

While early studies with Agrobacterium suggested that dicots were completely insensitive to this pathogen, those conclusions were based on lack of observable tumor formation in inoculated plants. More recently, it has been found that tumor formation in dicots is attributable to overproduction of auxins and cytokinins caused by the Ti plasmid, and therefore this symptom is not always a reliable indicator of transformation. More sensitive and more recent studies have shown production of opaline and nopaline, also attributed to the Ti plasmid, in Agrobacterium-inoculated monocots, and genetically engineered marker genes, such as GUS and NPTII, have been found in progeny of Agrobacterium-transformed corn plants. However, the successful and reliable use of this method still tends to be genotype specific both as to plants and Agrobacterium, as well as culture medium specific. Even under good conditions, the frequency of transformation is relatively low in some species.

In addition, Agrobacteria normally require a wound environment to induce the DNA transfer needed for transformation. For example, leaf punches and stem segments are commonly used because they present a cut and wounded surface to the bacteria that may contain cells capable of regenerating plants. There are times, however, when the intended target is an organized, multilayered tissue, such as a meristem, which is not readily accessible for Agrobacterium infection and transformation and is not easily wounded without damaging its organization and function. Even where leaf punches and stem segments are used, these only present a limited region, such as the perimeter of a leaf punch disk, which has been wounded. It would be desirable to use the entire surface of the disk as a potential transformation site.

Another method for transformation of plants has been bombardment of plant cells with dense microparticles carrying genetic material such as DNA sequences or plasmids. This method is less genotype specific, but frequencies of stable transformation are also low with this method. This is due in part to an absence of natural mechanisms to mediate integration of the introduced genetic material into the plant genome. In contrast, Agrobacterium species actively mediate those transformation events as a part of the natural process of infecting a plant cell. Thus, a continuing need exists for a method of transformation which reduces genotype specificity and enhances reliability, both in monocots and dicots.

DISCLOSURE OF THE INVENTION

This invention provides a method of applying bacteria to microparticles in such a manner that the bacteria retain their viability and virulence during the dry-down process associated with microparticle bombardment.

This invention permits the practice of an improved transformation method in which plant cells are bombarded with microparticles which carry an Agrobacterium species containing the genetic material of interest in its T-DNA. The Agrobacterium is thus able to attach to cells of tissues which have not been wounded and incorporate the genetic material permanently into the genome of those target cells at frequencies substantially higher than those achieved by conventional microparticle bombardment. This method allows transformation of organized tissues. Accordingly, the present invention provides a method for stable transformation of plant cells, comprising the steps of (a) preparing bacteria of an Agrobacterium species, which bacteria have been transformed to include in their T-DNA the genetic material to be inserted into the genome of the plant cells; (b) applying the bacteria to microparticles; and (c) subjecting the target tissue to microparticle bombardment using the microparticles to which the bacteria have been applied; whereby the bacteria introduced into the tissue can transfer the T-DNA, including the inserted genetic material, into the genome of viable cells in the tissue.

This method can be used to make permanently, heritably transformed plant cells which can be regenerated to whole, fertile plants. Of course, it will be appreciated that the foregoing method can also be used for transient transformations and transient assays in plant research.

The transformed plant cells produced by the practice of this invention are then suitable for regeneration by art-recognized techniques to produce whole, fertile plants which include in their nuclear genome the genetic material incorporated by the action of the bacteria. Accordingly, this invention also provides a method of producing whole, fertile, transformed plants, comprising the steps of (a) culturing tissues of the species and genotype to be transformed; (b) preparing bacteria of an Agrobacterium species, which bacteria have been transformed to include in their T-DNA the genetic material to be inserted into the genome of the plant cells; (c) applying the bacteria to microparticles; (d) subjecting the target tissue to microparticle bombardment using the microparticles to which the bacteria have been applied, whereby the bacteria incorporate the T-DNA, including the inserted genetic material, into the genome of the cells to produce transformed cells; and (e) regenerating the transformed cells thereby produced to produce whole plants.

Figure 2:
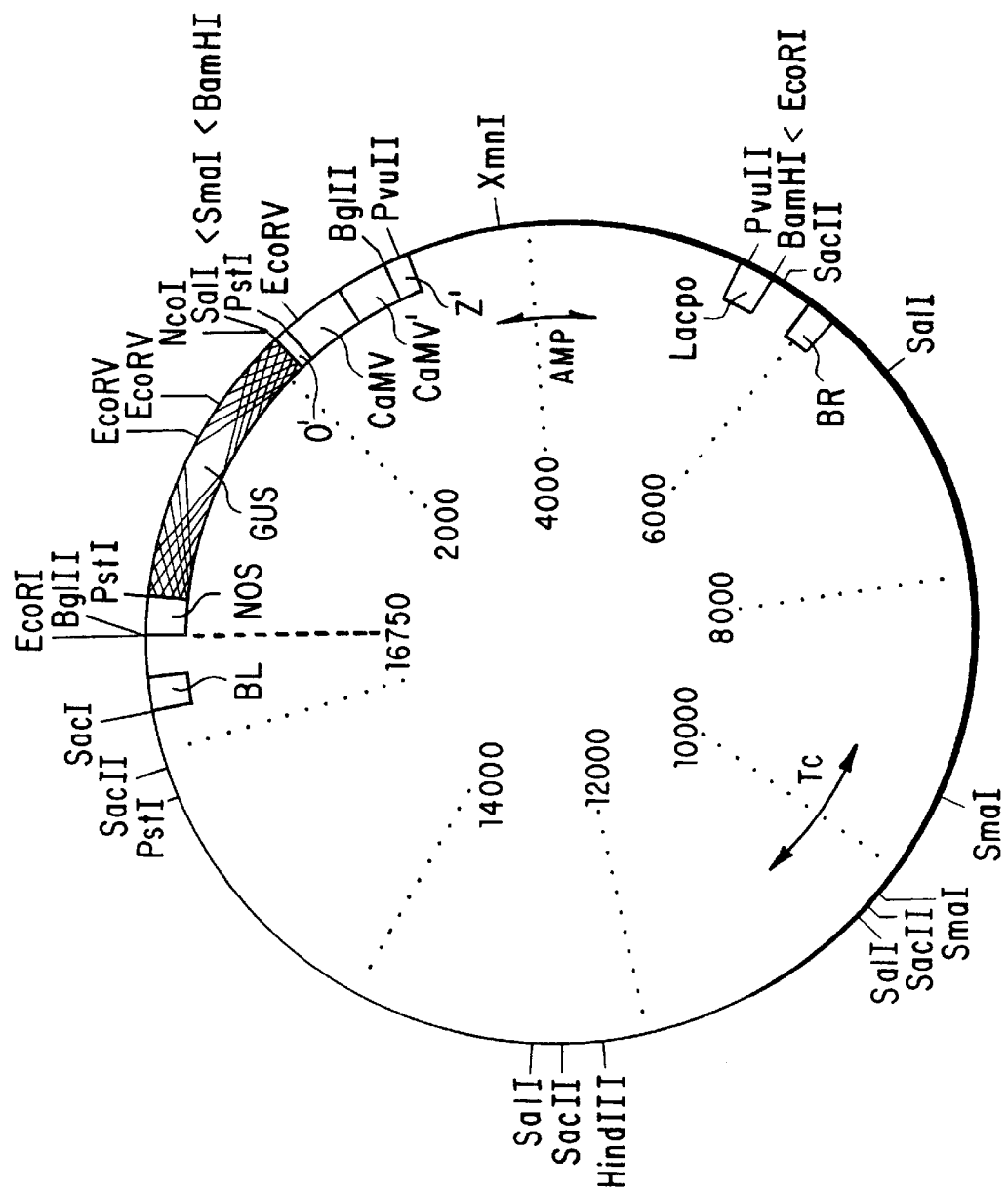

In many instances it will be desirable to regenerate plants from cultures which consist entirely or essentially of transformed cells, so that plants which are not chimeric can be obtained. This can be accomplished by growing the bombarded and Agrobacterium-treated tissue prior to regeneration in a selection medium in which only transformed cells are viable. This can be done by including a selectable marker gene such as kanamycin or Basta resistance in the plasmid to be inserted in the cells, as illustrated in FIG. 2. When the treated cells are grown in a medium containing the antibiotic or herbicide, the chemical will destroy non-transformed cells, and the surviving cultures will consist entirely of transformants, which can then be regenerated to produce plants which are not chimeric.

While not intending to be limited by theory, normal microparticle bombardment schemes require that individual or very small groups of particles enter the target cells in such a manner and location that the cells remain competent for division. In contrast, it is believed that Agrobacterium transformation occurs when the bacteria bind to the surface of a target cell. It is only the bacterial T-DNA from the Ti plasmid that is "injected" into the cell, once the bacteria are induced by the wound environment to activate their virulence and transfer functions. Thus it will be appreciated that the objective of bombardment in this invention is to induce cell wounding and death to a certain extent, rather than to minimize wounding as is desirable with the conventional practice of using particles loaded with naked plasmids. Once an area is damaged and releases the set of cell metabolites and wound exudates which Agrobacteria recognize, the remaining intact cells in the region of the wound are the transformation targets, rather than the cells which have been hit by particles. Accordingly, in the practice of this invention the cells which are struck by particles need not survive the bombardment step, and techniques for releasably adhering naked plasmids to microparticles need not be used.

Prior to work with this method of transformation, methods of applying Agrobacteria to microparticles were not available, but are important to the practice of the transformation technique of this invention. It has now been discovered that whole Agrobacteria can be successfully applied to particles in such a manner that they retain their activity when carried into plant tissues by microparticle bombardment. This method comprises the steps of (a) culturing the bacteria in a substantially full-strength culture medium comprising bactopeptone, yeast extract, and sodium chloride; (b) combining the bacteria in the medium with gold particles having a particle size of from about 0.6 to about 2.0 $\mu$m; and (c) air-drying the combined bacteria and particles for a period of from about 10 to about 15 minutes. Preferred full strength culture media are LB and YEP media, as described hereinafter. YEP medium is most preferred. Preferred gold particles are Engelhard A1570 Flakeless particles, which have a size distribution of from about 1.2 to about 1.5 $\mu$m.

Plants and Plant Cells

This method can be employed with any desired agronomic or horticultural species, including both monocots and dicots. As evidenced by the results achieved in sunflower, the higher transformation frequencies obtained with this invention can overcome in part the low frequencies of transformation associated with many difficult to transform genotypes and species. Preferably, the monocot species will be selected from maize, sorghum, triticale, barley, oats, rye, wheat, onion and rice, and the dicot species will be selected from soybean and other beans; alfalfa; tobacco, brassicas such as rapeseed, broccoli and cauliflower; sunflower; cucurbits such as melons, cucumbers and squashes; and solanaceae such as potatoes, peppers and tomatoes. Tissues from flowers, including orchid, rose, carnation, petunia, zinnia, aster, lily, marigold, impatiens, African and common violet and pansy, anthurium, gladiolus, hyacinth, geranium, lavender, peony, tulip, poppy, chrysanthemum, daffodil, and begonia varieties, as well as other ornamentals, including without limitation taxus, juniper, rhododendron, philodendron, ficus, ivy, pothos, lilac, cactus, dizygotheca, euphorbia, fatsia, hedera, coleus, and other varieties, and herbs such as parsley, sage, rosemary, thyme, basil, oregano, garlic, mint, fennel, marjoram, coriander, dill, and the like can also be subjected to the methods of this invention.

Tissues used can come from any desired plant part, including roots, anthers, stems, cotyledons, hypocotyls and flowers. Preferred tissues include meristem explants, whole leaf explants, partial leaf cuttings, leaf punch disks and immature embryos. An especially preferred tissue is a split meristem explant. This latter tissue has been described in the literature by B Schrammeijer et al., "Meristem Transformation of Sunflower via Agrobacterium," *Plant Cell Reports* 9: 55–60 (1990).

Agrobacterium Species

Species of Agrobacterium which can be used in plant transformation include *Agrobacterium tumefaciens* and *Agrobacterium rhizogenes*. Preferred is an *Agrobacterium tumefaciens* strain of the nopaline, binary type. Especially preferred is the publicly available *Agrobacterium tumefaciens* strain EHA101. This strain contains a C58 bacterial chromosome and a disarmed derivative of the Ti plasmid referred to in the literature as TiBO542. [See, e.g., Hood EE, Helmer GL, Fraley RT & Chilton M-D, "The Hypervirulence of Agrobacterium tumefaciensA281 is Encoded in a Region of TiBO542 Outside of T-DNA." *J. Bacteriology* 168:1291–1301 (1986)].

Figure 1:
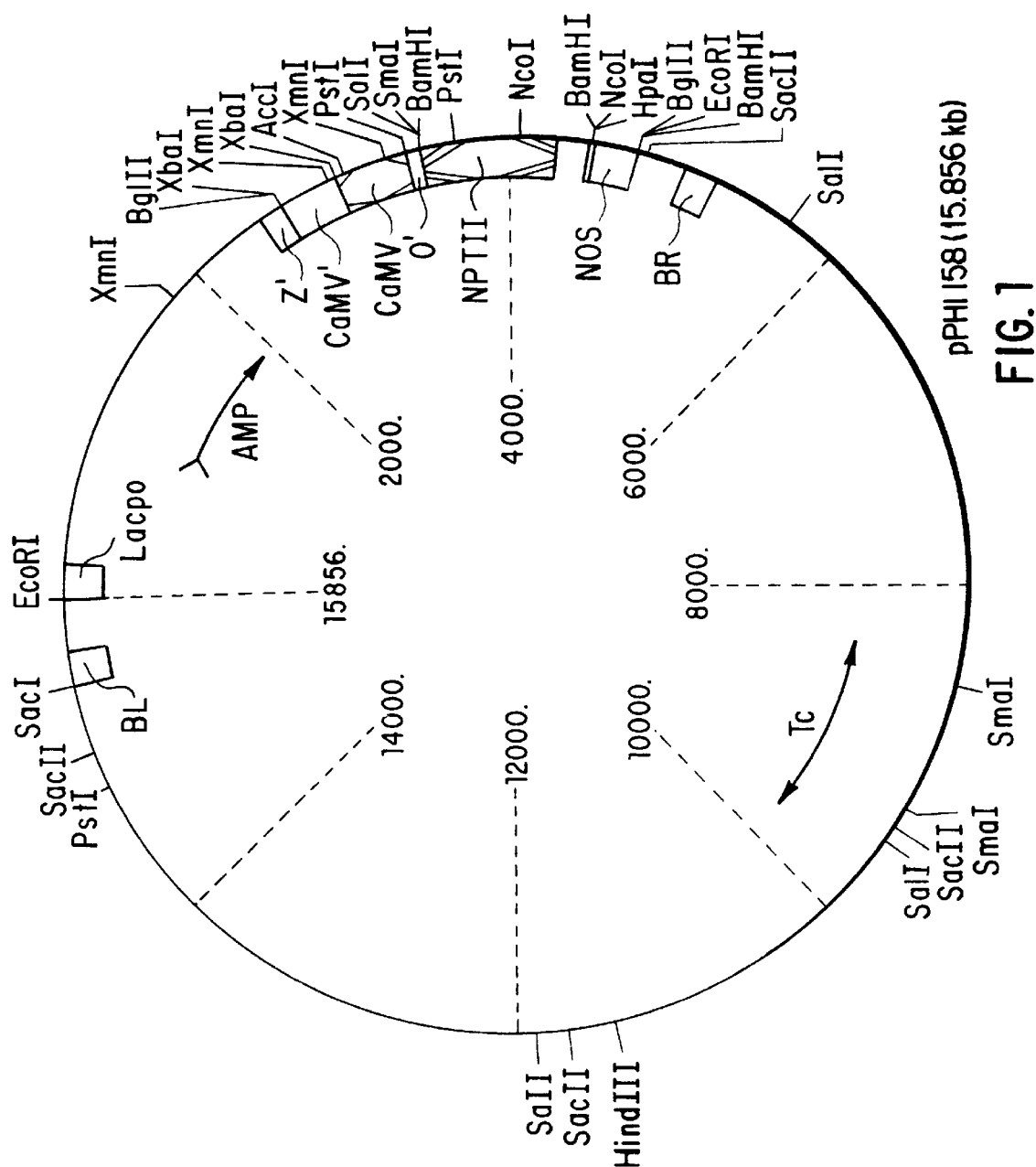
FIGS. 1 through 4 are plasmid maps of the plasmids pPHI158, pPHI167, pPHI419 and pPHI413, respectively.
Figure 3:
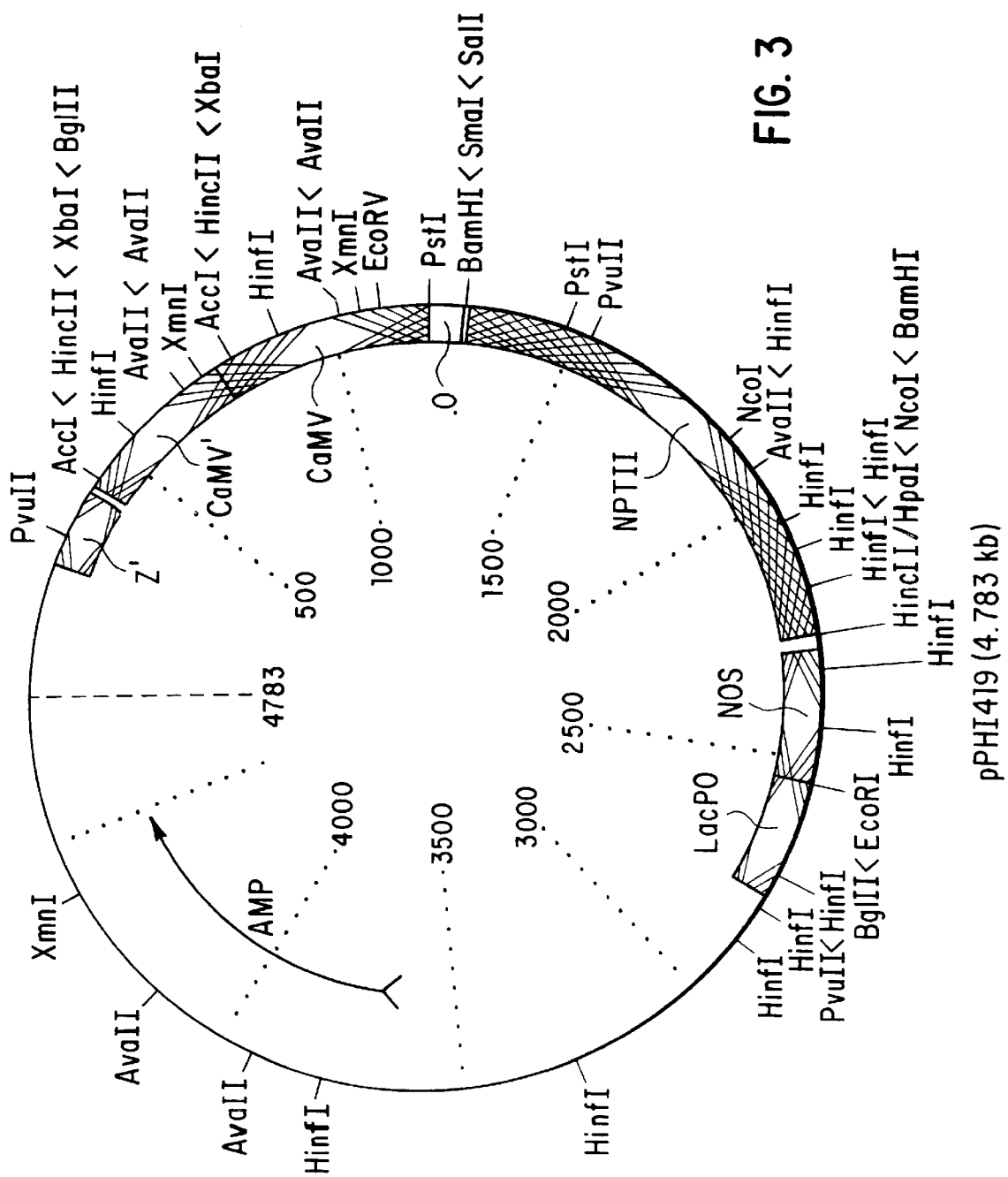
Figure 4:
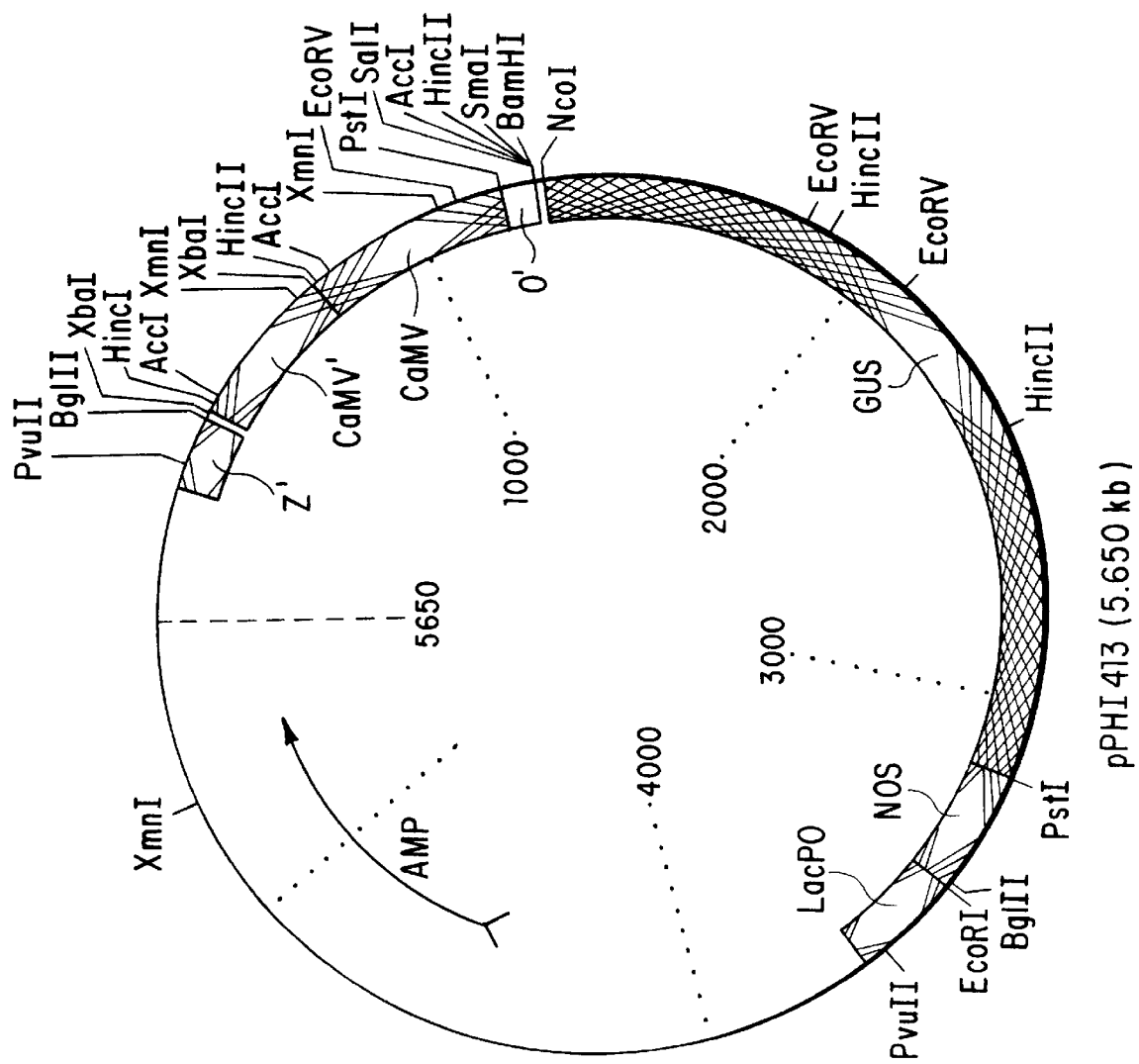

While selection and transformation of Agrobacterium does not per se form a critical part of this invention, in a preferred embodiment strain EHA101 is transformed with plasmids pPHI158 and pPHI167 as shown in FIGS. 1 and 2, using freeze-thaw transformation. pPHI158 (FIG. 1) is constructed by the insertion of linearized, EcoR1 digested plasmid pPHI419 (FIG. 3) carrying the plant-expressible marker NPTII near the right border of the 11.6 kb binary pPHI6. pPHI6 also contains the RK2 origin of replication and an ampicillin resistance marker. pPHI167 is constructed in an identical manner except that the linearized EcoR1 fragment of pPHI413 (FIG. 4) carrying the GUS gene is inserted into pPHI6. This is referred to in the literature as a binary vector system. [See, e.g., Hoekema A, Hirsch PR, Hooykaas PJJ & Schilperoort RA, "A Binary Plant Vector Strategy Based on Separation of Vir- and T-Regions of the A. tumefaciensTi Plasmid." *Nature* 303: 179–180 (1983).]

APPLYING BACTERIA TO PARTICLES

EXAMPLE I

A. tumefaciensEHA101 which was grown in YEP medium supplemented with 50 $\mu$g/mL kanamycin and 100

μg/mL carbenicillin to an $OD_{600}$ of 0.5–1.0 was resuspended in fresh YEP medium at various concentrations (as judged by OD readings) and different strengths of YEP. The bacteria were mixed with gold particles (Engelhard A1570 Flakeless) and applied as 1.5 μL droplets to macroprojectiles, where they were dried to a haze (about 10 minutes in the laminar flow hood) and then shot onto YEP plates. The plates were cultured and colonies growing back were counted as a method to quantitate bacterial viability after shooting.

| OD | YEP Concentration | # Colonies |
|---|---|---|
| 0.5 | 1/10 | 2.5 |
|  | 1/4 | 1 |
|  | 1/2 | 88 |
|  | full | 337 |
| 2.0 | 1/10 | 144 |
|  | 1/4 | 136 |
|  | 1/2 | 431 |
|  | full | 468 |

From these results it was determined that a full strength dry down medium was desirable to help survivability but that in a medium of appropriate strength, increasing concentrations of bacteria did not give proportional increases in the numbers of surviving colonies.

EXAMPLE II

A second series of experiments examined the role of dry down buffer and particle type in bacterial survivability after being shot from the particle gun. Compositions of media were as follows:

AB
 3 g/L $K_2HPO_4$
 1 g/L $NaH_2PO_4$
 1 g/L $NH_4Cl$
 0.3 g/L $MgSO_4$ $7H_2O$
 0.15 g/L KCl
 0.01 g/L $CaCl_2$
 2.5 mg/L $FeSO_4$ $7H_2O$
YEP
 10 g/L Yeast Extract
 10 g/L BactoPeptone
 5 g/L NaCl
LB
 5 g/L yeast extract
 10 g/L Bactopeptone
 10 g/L NaCl
all above at pH 7.0
Inoculation Buffer
 12.5 mM MES at pH 5.7
 1 g/L NH4Cl
 0.3 g/L MgSO4
Induction Buffer
 ¼-strength AB medium
 3% sucrose
 20 mM MES pH 5.5
 200 μM acetosyringone Results were as follows:

| Dry Down Medium | Particle Type | Avg. Colony # |
|---|---|---|
| Water | gold | 0 |
|  | tungsten | 0 |
| AB | gold | 8 |
|  | tungsten | 2.5 |
| Inoculation | gold | 26.5 |
|  | tungsten | 6 |
| Induction | gold | 53 |
|  | tungsten | 31 |
| LB | gold | 668 |
|  | tungsten | 363 |
| YEP | gold | 790 |
|  | tungsten | 384 |

From this it was determined that gold was markedly less toxic to the bacteria in the dried state than was tungsten and that the composition of the buffer was important as well.

EXAMPLE III

A third series of experiments were conducted along the lines of Examples I and II, but looked at time of dry down as a factor using the full strength YEP medium on gold particles (Engelhard A1570 Flakeless). Results were as follows:

| Dry down time | Number of Colonies |
|---|---|
| 0 minutes | 884 |
| 5 | too numerous to count |
| 10 | 457 |
| 15 | 489 |
| 20 | 252 |
| 30 | 223 |

The dry down time was the time of exposure to the air flow within laminar flow hood prior to shooting. The droplets were applied to the macroprojectiles at a volume of 1.5 μL. At 5 minutes the droplets were sticky and semi-dry while at 10 minutes they resembled a hazy powder that looked completely dry.

The foregoing experiment only measured viability as a function of dry-down. It should be understood that viability after dry-down does not imply or correlate directly with transformation ability. In other experiments, using bacteria with dry down times of less than 10 minutes did not produce transformed cells, although the bacteria were apparently viable.

EXAMPLE IV

Shelled sunflower seeds were surface sterilized with dilute hypochlorite solution and imbibed overnight (18 hours) in the dark at 26° C. on moist filter paper to initiate germination. The following morning, the cotyledons and the emerging root radical were removed and the explant containing the meristem is cultured overnight on medium 374B-GA, which contained Murashige & Skoog minerals, Shepard vitamins, 3% sucrose, 0.8% agar (Phytagar) and the hormones BAP (0.5 mg/L), IAA (0.25 mg/L) and GA (0.1 mg/L) at a pH of 5.6. 24 hours later the primary leaves were removed, exposing the apical meristem. The meristems were arranged in a 2 cm circle in the center of a petri plate containing a stiff water agar to hold the meristems upright for bombardment purposes. Separately, Agrobacterium tumefaciensEHA101/pPHI167 were cultured in full strength YEP medium and mixed with gold particles having a distribution of diameters of from 1.2 to 1.5 μm. 1.5 μL droplets of this mixture were applied to conventional macroprojectiles and dried for 10 to 15 minutes under a laminar flow hood. Using these projectiles, the meristems were bombarded twice in a microparticle bombardment apparatus of the general construction described by Sanford et al. in European Patent Application, Publication Number 331,885, claiming priority of U.S. patent application Ser. No. 161,807, filed Feb. 29, 1988, the disclosures of which are hereby incorporated herein by reference. Transformation was evaluated by counting stained sectors after treatment with x-gluc. Results were as follows:

| No. of Meristems | Transformed Sectors | % |
|---|---|---|
| 121 | 4 | 3.3 |
| 125 | 3 | 2.4 |

What is claimed is:

1. A method for transformation of cells of an Agrobacterium-transformable plant by inserting genetic material into the genome of the cells, comprising the steps of
   (a) adhering bacteria of an Agrobacterium species, which bacteria have been transformed to include in their T-DNA the genetic material to be inserted into the genome of the cells to microparticles;
   (b) subjecting a tissue from the plant to microparticle bombardment using the microparticles to which the bacteria have been adhered;
   (c) permitting the bacteria to attach to cells within the tissue and transfer their T-DNA, including the inserted genetic material, into the genome of the cells and;
   (d) selecting for transformed cells.

2. A method according to claim 1 wherein the tissue is a meristem explant.

3. A method according to claim 1 wherein the tissue is a member selected from the group consisting of whole leaf explants, partial leaf cuttings, and leaf punch disks.

4. A method according to claim 1 wherein the tissue is an immature plant embryo.

5. A method according to claim 1 wherein the plant is a monocot selected from the group consisting of maize, sorghum, triticale, barley, oats, rye, wheat, onions and rice.

6. A method according to claim 1 wherein the plant is a dicot selected from the group consisting of soybean, alfalfa, tobacco, brassicas, sunflower, cucurbits, potatoes, peppers and tomatoes.

7. A method of producing whole plants of a selected, Agrobacterium-transformable species, the cells of which have been transformed by insertion of genetic material into their genome, comprising the steps of
   (a) adhering bacteria of an Agrobacterium species, which bacteria have been transformed to include in their T-DNA the genetic material to be inserted into the genome of the cells, to microparticles;
   (b) subjecting a regenerable tissue from the transformable plant species to be transformed to microparticle bombardment using the microparticles to which the bacteria have been adhered;
   (c) permitting the bacteria to incorporate their T-DNA, including the inserted genetic material, into the genome of cells of the regenerable tissue to produce transformed, regenerable cells;
   (d) selecting for transformed cells and;
   (e) regenerating whole plants from the transformed cells.

8. A method according to claim 7, further comprising the step of growing the bombarded tissue in a selection medium in which only transformed cells are viable, prior to regeneration.

9. A method of adhering bacteria of the genus Agrobacterium to microparticles in such a manner that they retain their viability when carried into plant tissues by microparticle bombardment, comprising the steps of:
   (a) culturing the bacteria in a full-strength culture medium comprising bactopeptone, yeast extract, and sodium chloride;
   (b) combining the bacteria in the medium with gold particles having a particle size of from about 0.6 to about 2.0 μm; and
   (c) air-drying the combined bacteria and particles for a period of from about 10 to about 15 minutes.

10. A method according to claim 9 wherein the culture medium consists essentially of from about 5 g/L to about 10 g/L yeast extract; about 10 g/L bactopeptone; and from about 5 g/L to about 10 g/L NaCl pH 7.0.

11. A method according to claim 9 wherein the combined bacteria and particle are dried onto macroprojectiles.

* * * * *